United States Patent
Anderson

(10) Patent No.: US 7,068,051 B2
(45) Date of Patent: Jun. 27, 2006

(54) PERMITTIVITY MONITOR USES ULTRA WIDE BAND TRANSMISSION

(75) Inventor: Scott K. Anderson, Meridian, ID (US)

(73) Assignee: Technical Development Consultants, Inc., Meridian, ID (US)

(*) Notice: Subject to any disclaimer, the term of this patent is extended or adjusted under 35 U.S.C. 154(b) by 0 days.

(21) Appl. No.: 10/905,417

(22) Filed: Jan. 3, 2005

(65) Prior Publication Data

US 2005/0088182 A1 Apr. 28, 2005

Related U.S. Application Data

(63) Continuation-in-part of application No. 10/367,688, filed on Feb. 19, 2003, now abandoned.

(60) Provisional application No. 60/534,293, filed on Jan. 5, 2004.

(51) Int. Cl.
  *G01R 27/04* (2006.01)
  *G01R 27/32* (2006.01)

(52) U.S. Cl. ...................... 324/640; 324/639
(58) Field of Classification Search ............. 324/640, 324/639, 663, 664
See application file for complete search history.

(56) References Cited

U.S. PATENT DOCUMENTS

| | | | | |
|---|---|---|---|---|
| 5,673,050 A | * | 9/1997 | Moussally et al. | 342/22 |
| 5,677,476 A | * | 10/1997 | McCarthy et al. | 73/29.01 |
| 5,818,241 A | * | 10/1998 | Kelly | 324/640 |
| 6,466,168 B1 | * | 10/2002 | McEwan | 342/465 |
| 6,657,443 B1 | * | 12/2003 | Anderson | 324/664 |
| 2003/0024155 A1 | * | 2/2003 | Kuroda et al. | 47/1.01 R |
| 2004/0239337 A1 | * | 12/2004 | Jean et al. | 324/638 |

* cited by examiner

*Primary Examiner*—Diane Lee
*Assistant Examiner*—John Teresinski
(74) *Attorney, Agent, or Firm*—Your Intellectual Property Matters; Robert A. Frohwerk

(57) ABSTRACT

Narrow pulses transmitted wirelessly from a transmitting antenna to a receiving antenna are used to measure the electrical permittivity of the medium of interest between the two antennas. Timing signals are transmitted along a shielded transmission line coincident with the wireless transmission through the medium. The received waveform is digitized in the time domain and analyzed to determine the propagation time. The effects of dispersion caused by the conductive and dielectric properties of the medium on the transmitted waveform are overcome through analysis of the digitized waveform, resulting in an accurate measurement of the propagation time and thus the permittivity of the medium, from which volumetric moisture content may be derived.

23 Claims, 3 Drawing Sheets

PERMITTIVITY MONITOR USES ULTRA WIDE BAND TRANSMISSION

CROSS-REFERENCES TO RELATED APPLICATIONS

This application is a Continuation-in-Part of U.S. patent application Ser. No. 10/367,688, filed Feb. 19, 2003, entitled "Method and Apparatus for Determining Moisture Content and Conductivity," now abandoned, which is incorporated herein by reference. In addition, this application claims the benefit of U.S. Provisional Application Ser. No. 60/534,293, filed Jan. 5, 2004, entitled "Permittivity Monitor."

STATEMENT REGARDING FEDERALLY SPONSORED RESEARCH OR DEVELOPMENT

Not Applicable.

FIELD OF THE INVENTION

The present invention relates generally to electronic moisture sensors. In particular the described invention relates to a means of deriving moisture content of a medium based upon measurement of its permittivity. An ultra wide band transmission is used to measure permittivity with reliance upon certain techniques disclosed in U.S. Pat. No. 6,657,443 as those techniques are applied in a wireless manner to a topology that is related to but distinct from those described in U.S. Pat. No. 6,831,468.

BACKGROUND OF THE INVENTION

The measurement of soil moisture at various depths in the soil is an increasingly important activity in modern agriculture. Crop yields are improved, water and fertilizer are conserved, and diseases are prevented when irrigation water is applied in a manner that avoids stress to a crop. One cause of crop stress is allowing the soil to become too dry. Other stress factors are root asphyxiation and excessive leeching of nutrients due to over-watering. Soil moisture measurements taken at various soil depths provide the necessary feedback to facilitate precise scheduling of irrigation.

A variety of sensors have been developed to detect moisture in various media. These include conductivity sensors and sensors of bulk dielectric constant. Methods used for measuring the dielectric constant include time domain reflectometry or transmissometry, frequency domain reflectometry (FDR), capacitance probe (CP), and ground-penetrating radar (GPR). These methods exploit the high dielectric constant of water relative to that of the medium being measured in order to extrapolate the moisture content of the medium.

Soil permittivity measurements have become the standard means of deriving soil moisture content. Time Domain Reflectometer (TDR) and Time Domain Transmissometer (TDT) devices have been developed for use in soil moisture studies. Recent advances using low cost digital signal processing in conjunction with these devices has yielded high accuracy and stability even in the presence of temperature variations and moderate concentrations of salts and other ionic material in the soil. Reference is made to U.S. Pat. Nos. 6,657,443 and 6,831,468. Time Domain Transmissometers are well suited for permanent installation where continuous moisture monitoring is needed for closed-loop irrigation control. They are not well suited for probing-type measurements because they cannot be installed in the soil without excavation. This hindrance arises from the fact that the transmission line attached to the device is in the form of a loop and is not easily inserted into the soil. In contrast, Time Domain Reflectometers typically have an open-ended transmission line. The ends of the two-wire line can be sharpened such that insertion into the soil becomes practical without excavation. Thus probing-type measurements can readily be taken with a TDR probe but only at the depth that the fixed transmission line will allow.

Crop growers need soil moisture data throughout the root zone and also in the subsoil. Devices have been developed that are inserted into a PVC pipe-lined bore hole which measure the capacitance of the electric circuit formed by the plastic pipe wall thickness and a volume of soil outside the pipe. Cylindrically-shaped capacitor plates inside the pipe define the capacitor geometry. These plates can be moved up and down inside the pipe to take capacitance readings at various depths. The capacitance readings can then be related to moisture content. The electric field in the soil outside the pipe is distorted by conductive losses in the soil causing the output reading to be dependent on soil chemistry. Hence the devices are used in a relative mode, that is, they must be calibrated for the soil in which they are inserted and the readings must be referenced to that calibration point. If the soil chemistry changes due to salts or fertilizer content of the soil, then the calibration becomes invalid. The accuracy of such devices is also inferior to the TDR and TDT devices discussed above.

Current electronic methods used for monitoring soil moisture are subject to errors caused by compaction, electrical conductivity and temperature of the soil. Sensing devices must be calibrated for the soil and the readings must be interpreted by someone trained in the use of the specific sensing device. The improved sensor of the presently described invention reports absolute soil moisture at any desired soil depth. This improved sensor does not need to be calibrated for the soil. Its readings are stable with changing soil temperatures, electrical conductivity and compaction. The resulting data may be easily and reliably used by the crop grower without need of a consultant to interpret the readings. The data is of sufficient accuracy and stability that automatic, closed-loop irrigation scheduling may become the standard practice among early-adopting growers.

BRIEF SUMMARY OF THE INVENTION

The disclosed invention relates to the precise measurement of the dielectric constant, or permittivity, of a bulk medium such as soil, lumber, paper pulp, grain, foods in process, and more. The disclosed approach differs from many other methods of measuring moisture content in that the dielectric constant of the material being analyzed can be determined without disturbing the medium. Knowledge of the dielectric constant then allows one to calculate the moisture content of the medium. This calculation may use the Topp equation, or the dielectric mixing equation involving the square root of the sum of the squares of the component dielectrics, or some other relationship appropriate to the medium in question, where those familiar with the art surrounding the various media will recognize suitable equations.

In the preferred embodiment of the present invention a very narrow, high energy pulse is transmitted through the medium from a pulse transmitting device at one location to a receiving device at another location where the distance between the transmitter and receiver is precisely known. The pulse propagates through the medium without the use of a transmission line or waveguide. Appropriate technical literature has shown that by measuring the propagation time of the pulse through the medium over a known distance, its permittivity can be readily determined from:

$$t_{pd} = l\sqrt{\mu \in}$$ [Equation 1], where $t_{pd}$ is the propagation time through the medium, l is the effective distance between transmitter and receiver, $\mu$ is the permeability of the medium and $\in$ is its permittivity.

A very narrow pulse with fast rise and fall times has a broad spectral content with uniform amplitude, sin(x)/x distribution, across its spectrum. When transmitted from a broadband antenna, such a pulse propagates as an electromagnetic wave through any medium that is either non-conductive or of low conductivity. The antennas act as high-pass filters, removing the lower frequency and direct current components, resulting in a doublet waveform from the receiving antenna. This simplifies the requirements of the broadband transmitting and receiving antennas and also narrows the spectrum for preservation of group delay. The low-side truncated spectrum facilitates efficient wireless propagation while preserving high frequency characteristics from which propagation time and rise time degradation can be measured.

As in U.S. Pat. No. 6,657,443 a very precise timing and successive approximation amplitude-measuring scheme captures the timing of the received waveform with picosecond resolution and its amplitude with millivolt resolution. From point-by-point measurements, the characteristic received waveform may be examined to determine its propagation delay. This information is used to infer the bulk dielectric constant of the moisture-bearing medium. Other characteristics of the received waveform, particularly rise time degradation, may be used to infer conductivity of the medium under test. Although reconstruction of the entire waveform is not necessary, such detail is useful in the waveform processing algorithms to insure that the desired information-bearing features are properly identified.

DETAILED DESCRIPTION OF THE INVENTION

Use of the Time Domain Reflectometry (TDR) techniques disclosed in U.S. Pat. No. 6,831,468 allow for a physical separation of the transmitting and receiving unit of U.S. Pat. No. 6,657,443. An embodiment of the present invention results when the unshielded transmission line of '468 that would normally be immersed in the medium being measured is replaced by a wireless connection using a transmitter and receiver antenna pair.

Figure 1:
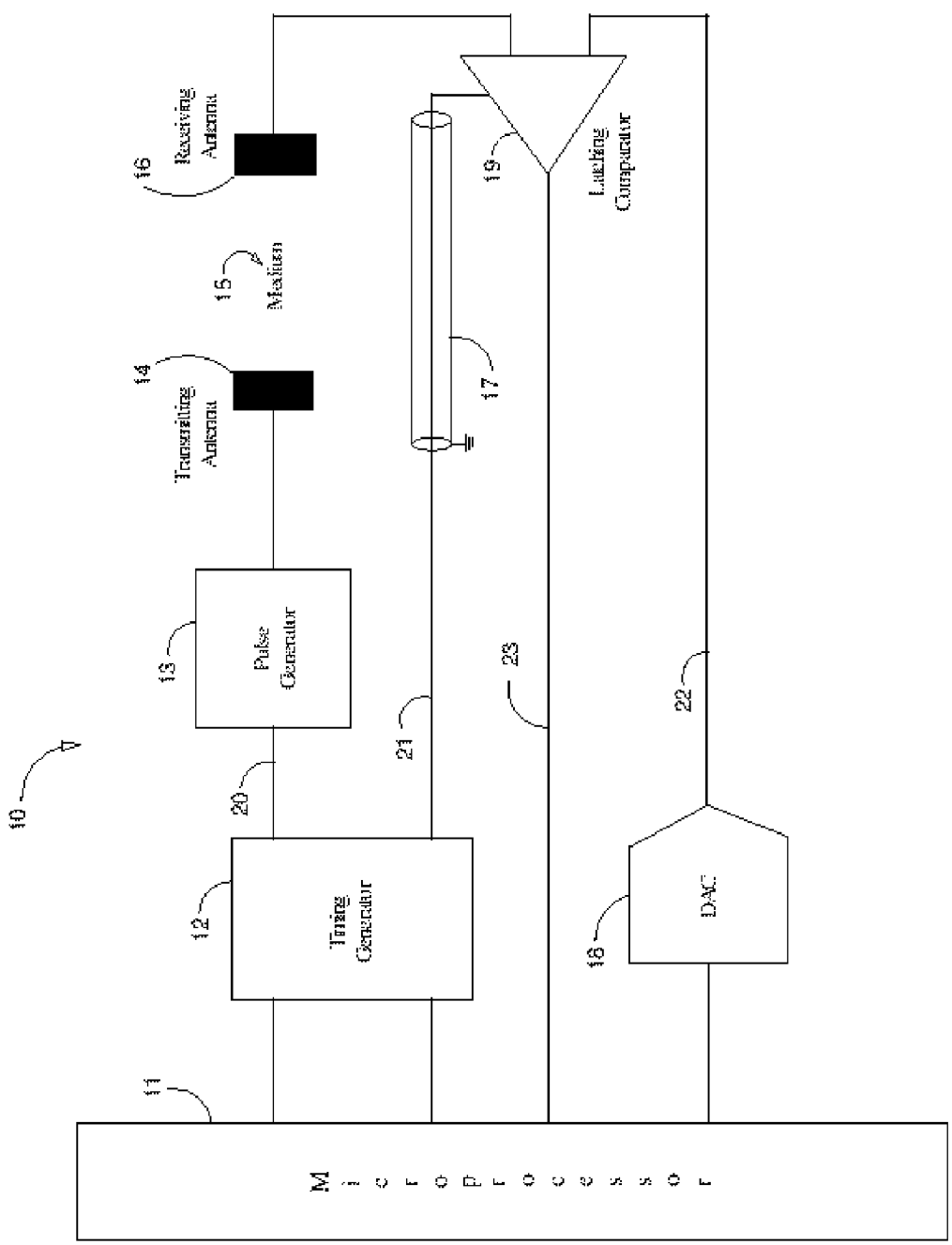
FIG. 1 is a simplified block diagram of an ultra wideband permittivity monitoring system under the present invention.

FIG. 1 is a representation of an embodiment of a Permittivity Monitor 10 of the present invention. The pulse transmitter in this system comprises a pulse generator 13 that drives a broadband transmitting antenna 14 with narrow pulses. Each pulse can be generated by first generating a fast transitioning step function using a step recovery diode, an avalanche transistor, a GaAs transistor, a SiGe transistor or other ultra fast device. The step function can then be converted to a narrow pulse using a shorted transmission line stub connected across the step function output. A high pass filter may also be incorporated in the pulse output circuitry to remove the spectral content below several hundred megahertz but antennas themselves perform this function rendering the additional filter hardware unnecessary. The transmitting and receiving antennas, 14 and 16 respectively, can be connected through wideband transformers or baluns to electrically isolate the system from the medium being measured.

The pulse receiver comprises a broadband receiving antenna 16 and an ultra-high-speed latching comparator 19. The latching comparator 19 receives its latch trigger over shielded cable 17. The latching comparator 19 holds the logical state of the comparator input, presented to it by receiving antenna 16, with respect to the reference input at the precise time of the latching signal. Thus, latching comparator 19 acts as a logical sample and hold system that preserves the condition of its input being greater or less than the reference input at the time of the latching signal.

A precise programmable offset timing generator 12 triggers both the pulse generator 13 and the receiving latching comparator 19. This generator produces two output transitions that are spaced by a precisely timed programmable interval. The first transition, on line 20, causes the pulse generator 13 to emit a pulse. The second transition, on line 21, is injected into shielded cable 17 to latch the state of the response to the first pulse relative to a reference setting 22 into the output of the latching comparator 19. Reference setting 22 is established by the Digital-to-Analog Converter (DAC) 18. The microprocessor 11 then reads the state of latching comparator 19 to determine whether or not any portion of a waveform greater than a reference setting appeared at the input of latching comparator 19 at the time of the latching transition received through shielded cable 17. The position in time of the received pulse can be determined by successively emitting pulses from the pulse generator 13 and latching responses in the latching comparator 19 at successively changing timing intervals between the two transitions. After the launch of each transition pair, the output of the latching comparator 19 is examined by the microprocessor to determine if a signal level greater than the pre-programmed reference level established by DAC 18 was detected. Its amplitude can be measured through a successive approximation technique that involves successively setting DAC 18 at each programmed transition spacing interval. This technique along with the operation of the programmable offset timing generator is disclosed in '443. This process results in a set of digitized data points that describe appropriate portions of the received waveform 30.

Figure 2:
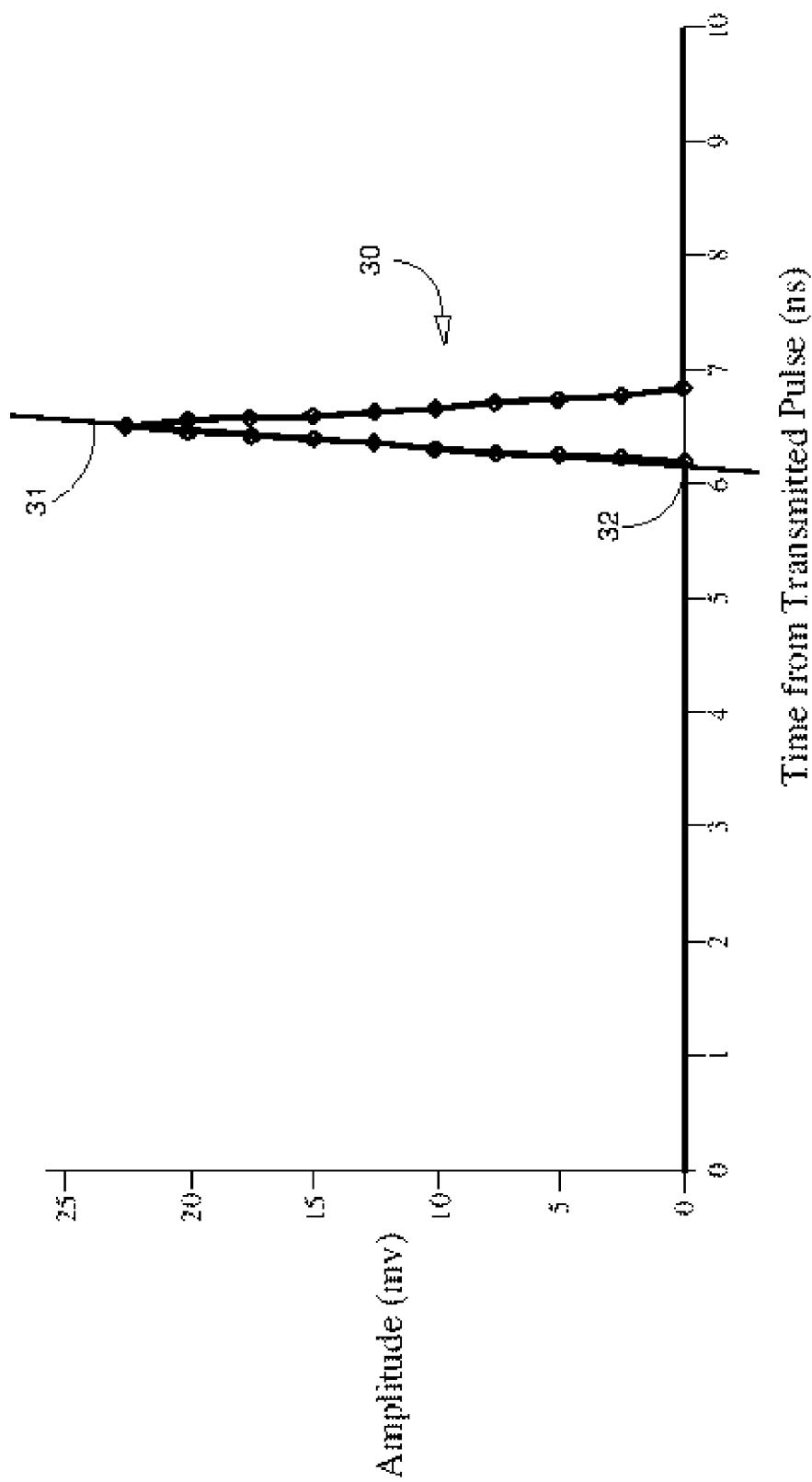
FIG. 2 depicts a typical waveform encountered in an ultra wideband permittivity monitoring system.

Received waveform 30 is depicted in FIG. 2 after it has been digitized. Since the antennas cannot propagate the low frequency portions of the impulse spectrum, they act as high pass filters and thus differentiate the signal. Therefore, the signal received as 30 is a reduced amplitude second derivative of the transmitted signal.

The true propagation time for the waveform in FIG. 2 is the time where the first transmitted energy appears at the receiver, that is, the lower left side of the depicted waveform where it breaks from the time axis. That time can be found by projecting a tangent line 31 through the points representing the rising edge of the waveform and projecting that line down to the time axis. The point of intersection 32 with the time axis represents the propagation time. The technique for that process has been described in '443. Soil permittivity can be derived from the time of propagation delay extracted from the waveform by knowing the distance through which the propagated wave had traveled through the soil. Amplitude attenuation along with the propagation delay can be used to determine conductivity of the medium.

Figure 3:
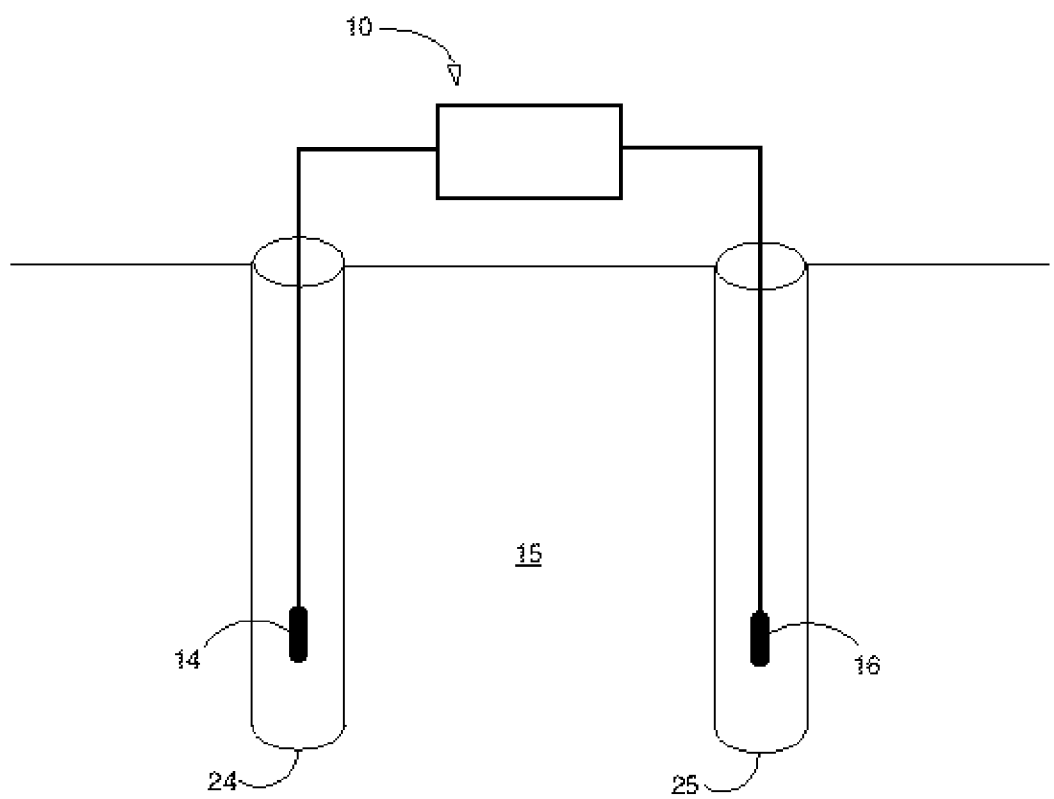
FIG. 3 shows a typical application of an ultra wideband permittivity monitoring system when used to measure soil moisture content.

The use of the device for measurement of moisture at various depths in the soil is shown in FIG. 3 where the transmitting and receiving antennas, 14 and 16 respectively, have been inserted into holes 24 and 25 which have been bored into the soil. To avoid collapse of the bored holes 24 and 25, they will typically be lined, often with PVC pipe. By moving the antennas vertically in the bore holes 24 and 25 of FIG. 3, permittivity and hence moisture content can be determined at various soil depths.

An alternative means to derive a moisture profile versus depth is to use multiple antenna elements on fixed transmit and receive stakes. The elements can be switched using PIN diodes so that only one transmit and one receive element are active at a given time. The soil moisture content can then be derived for the soil between the two active elements. By switching active antenna elements up and down the stakes, the soil moisture reading can be derived at the various depths where those antenna elements are present.

In one practical use the present invention will measure the permittivity of a soil sample as a means of determining its moisture content. This embodiment will have transmitting and receiving units connected by a length, say 1.5 meters, of coaxial cable (as 17) with associated power and sensing lines. Two sections of PVC pipe will be inserted vertically into the ground at a measured spacing of, for example, 0.6 meters. Due to the high frequency of the spectrum being used, the antenna stubs (14 and 16) are very small, allowing the transmitting and receiving units to be packaged into small probes. These units will then be lowered into the ground, one into each of the PVC pipe sections with the cable 17 lying above ground. The user interface, best associated with the microprocessor 11 at the transmitting unit, will have been calibrated to account for the length of the cable 17, and will adjust measurements to account for an input value of the measured spacing between the two PVC sections. Since the probes are small, they may be lowered below the surface to known depths in order to profile the permittivity and computed moisture content of the soil as a function of depth below the soil surface.

A second practical use of a preferred embodiment allows for measurement of moisture content of a stack of lumber in a warehouse or drying kiln without disturbing or separating the stack. The transmitting and receiving probes are placed one each on opposite sides of the stack, perhaps one above and the other below. The measurement will be of the average moisture content of the stack of lumber.

A third of many possible applications of the present invention can provide real-time measurement of the moisture content of grain as it is being processed by a combine in the field. With transmitting and receiving probes suitably located in a grain chute, the moisture of the passing grain can be determined. If the measured level exceeds some threshold, the harvest operation may be suspended to allow the field to continue to dry. Alternately, the load of grain can be tagged with its moisture content and sent to appropriate storage for further drying.

While the present invention has been described with respect to a preferred embodiment, there is no implication to restrict the present invention to preclude other implementations that will be apparent to those skilled in the related arts. It is easily recognized that the described invention may be implemented with a variety of components, operating over a wide range of frequencies, and in various topologies adapted to a multitude of applications. Therefore, it is not intended that the invention be limited to the disclosed embodiments or to the specifically described details insofar as variations can be made within the spirit and scope of the appended claims.

What is claimed is:

1. An apparatus for measuring permittivity of a medium, the apparatus comprising:
    (a) an ultra wide band transmitter for wirelessly transmitting an electromagnetic waveform through said medium;
    (b) an ultra wide band receiver for wirelessly receiving a resultant waveform through said medium in response to the transmitter;
    (c) a measurement means for measuring amplitude of the resultant waveform as a function of time, the measurement means comprising an implementation of a real-time digitizer using a successive approximation technique;
    (d) a synchronization means for synchronizing the measurement means with the transmitter; and
    (e) a means of analysis for extracting characteristic features of the resultant waveform to determine the permittivity of said medium.

2. The apparatus of claim 1, wherein said means of analysis comprises:
    an interface with the measurement means and with the synchronization means for determination of a time of propagation through said medium; and
    a calculation means for deriving permittivity of said medium from the determined time of propagation.

3. The apparatus of claim 1, wherein said means of analysis comprises:
    an interface with the measurement means and with the synchronization means for determination of amplitude attenuation of the resultant waveform; and
    a calculation means for deriving conductivity of said medium from the determined amplitude attenuation.

4. The apparatus in claim 1, wherein said medium is soil.

5. The apparatus in claim 1, wherein said medium is bulk grain.

6. The apparatus in claim 1, wherein said medium is lumber.

7. The apparatus in claim 1, wherein said medium is bulk paper.

8. The apparatus in claim 1, wherein said medium is paper pulp.

9. The apparatus in claim 1, wherein said medium is a hydrocarbon fuel.

10. The apparatus in claim 1, wherein said medium is oil.

11. A method of determining permittivity of a moisture-bearing medium, comprising the steps of:
    (a) providing a transmitting antenna to wirelessly transmit an ultra wide band electromagnetic waveform into the medium;
    (b) providing a receiving antenna for wireless reception through the medium of a resultant waveform in response to the wirelessly transmitted waveform;
    (c) providing a latching comparator connected to said receiving antenna;
    (d) providing a shielded transmission line connected to said latching comparator;
    (e) applying the ultra wide band electromagnetic waveform to said transmitting antenna;
    (f) digitizing portions of the resultant waveform in real-time by successive approximation; and (g) extracting pertinent characteristic features from which the permittivity can be determined.

12. The method in claim 11 wherein the step of digitizing further comprises the steps of:
   (a) providing a programmable voltage reference to which the resultant waveform is compared by said latching comparator;
   (b) providing a programmable time offset for generation of a precisely-timed sampling strobe after the applying of the ultra wide band electromagnetic waveform in order to sample the amplitude of the resultant waveform at said latching comparator, the sampling strobe being sent through said shielded transmission line to said latching comparator;
   (c) inserting a multiplicity of the ultra wide band electromagnetic waveform into said transmitting antenna and adjusting the programmable voltage reference in the manner of a successive approximation until an amplitude representative of a composite of the resultant waveform at the programmed point in time has been acquired; and
   (d) changing the programmable time offset to a next desired point in time and repeating the step of inserting in order to acquire another amplitude representative of a multiplicity of the resultant waveform at said next desired point in time until said portions of the resultant waveform have been digitized.

13. The method in claim 11, wherein the step of extracting pertinent characteristic features, comprises the steps of:
   (a) determining a characteristic slope of transition from a subset of measured points which represent that portion of the resultant waveform which contains a response to the first transmitted energy at the receiver;
   (b) locating a point of maximum slope of transition from within said subset of measured points;
   (c) projecting a straight line having said characteristic slope of transition through said point of maximum slope to a baseline reference level; and
   (d) finding an intercept point of said straight line at said baseline reference level, wherein the time associated with said intercept point represents said propagation time of the ultra wide band waveform through the medium.

14. The method in claim 13, wherein said propagation time is used to calculate a value for the permittivity of the medium through which the ultra wide band electromagnetic waveform was wirelessly transmitted.

15. The method in claim 13, wherein said characteristic slope of transition of the resultant waveform is used to determine a value for the conductivity of the medium through which the ultra wide band electromagnetic waveform was wirelessly transmitted.

16. The method in claim 13, wherein the medium is soil.

17. The method in claim 11, wherein the medium is soil.

18. The method in claim 11, wherein the medium is bulk grain.

19. The method in claim 11, wherein the medium is lumber.

20. The method in claim 11, wherein the medium is bulk paper.

21. The method in claim 11, wherein the medium is paper pulp.

22. The method in claim 11, wherein the medium is a hydrocarbon fuel.

23. The method in claim 11, wherein the medium is oil.

* * * * *